United States Patent
Malaviya et al.

(10) Patent No.: US 7,914,808 B2
(45) Date of Patent: Mar. 29, 2011

(54) HYBRID BIOLOGIC/SYNTHETIC POROUS EXTRACELLULAR MATRIX SCAFFOLDS

(75) Inventors: Prasanna Malaviya, Ft. Wayne, IN (US); Mora C. Melican, Bridgewater, NJ (US); Alireza Rezania, Hillsborough, NJ (US); Iksoo Chun, Flemmington, NJ (US)

(73) Assignee: DePuy Products, Inc., Warsaw, IN (US)

( * ) Notice: Subject to any disclaimer, the term of this patent is extended or adjusted under 35 U.S.C. 154(b) by 778 days.

(21) Appl. No.: 10/195,341

(22) Filed: Jul. 15, 2002

(65) Prior Publication Data

US 2003/0021827 A1    Jan. 30, 2003

Related U.S. Application Data

(60) Provisional application No. 60/388,711, filed on Jun. 14, 2002, provisional application No. 60/305,786, filed on Jul. 16, 2001.

(51) Int. Cl.
*A61F 2/00* (2006.01)
(52) U.S. Cl. .......................... 424/423; 424/422
(58) Field of Classification Search .................. 424/423, 424/426; 623/11.11
See application file for complete search history.

(56) References Cited

U.S. PATENT DOCUMENTS

| | | |
|---|---|---|
| 3,075,961 A | 1/1963 | Veis et al. |
| 3,272,204 A * | 9/1966 | Artandi et. al. .............. 606/151 |
| 3,562,820 A | 2/1971 | Braun |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,205,399 A | 6/1980 | Shalaby et al. |
| 4,208,511 A | 6/1980 | Shalaby et al. |
| 4,352,463 A | 10/1982 | Baker |
| 4,400,833 A | 8/1983 | Kurland |
| 4,418,691 A | 12/1983 | Yannas et al. |
| 4,610,397 A | 9/1986 | Fischer et al. |
| 4,642,120 A | 2/1987 | Nevo et al. |
| 4,669,473 A | 6/1987 | Richards et al. |
| 4,703,108 A | 10/1987 | Silver et al. |
| 4,705,040 A | 11/1987 | Mueller et al. |
| 4,741,330 A | 5/1988 | Hayhurst |
| 4,750,492 A | 6/1988 | Jacobs |
| 4,873,976 A | 10/1989 | Schreiber |
| 4,880,429 A | 11/1989 | Stone |
| 4,902,508 A | 2/1990 | Badylak et al. |
| 4,919,667 A | 4/1990 | Richmond |
| 4,956,178 A | 9/1990 | Badylak et al. |
| 4,956,179 A | 9/1990 | Bamberg et al. |
| 4,976,715 A | 12/1990 | Bays et al. |
| 5,007,934 A | 4/1991 | Stone |
| 5,061,286 A | 10/1991 | Lyle |
| 5,102,421 A | 4/1992 | Anspach, Jr. |
| 5,108,438 A | 4/1992 | Stone |
| 5,116,374 A | 5/1992 | Stone |
| 5,128,326 A | 7/1992 | Balazs et al. |
| RE34,021 E | 8/1992 | Mueller et al. |
| 5,236,431 A | 8/1993 | Gogolewski et al. |
| 5,246,441 A | 9/1993 | Ross et al. |
| 5,258,015 A | 11/1993 | Li et al. |
| 5,269,809 A | 12/1993 | Hayhurst et al. |
| 5,275,826 A | 1/1994 | Badylak et al. |
| 5,281,422 A | 1/1994 | Badylak et al. |
| 5,306,311 A | 4/1994 | Stone et al. |
| 5,320,633 A | 6/1994 | Allen et al. |
| 5,350,583 A | 9/1994 | Yoshizato et al. |
| 5,352,463 A | 10/1994 | Badylak et al. |
| 5,372,821 A | 12/1994 | Badylak et al. |
| 5,374,268 A | 12/1994 | Sander |
| 5,376,118 A | 12/1994 | Kaplan et al. |
| 5,380,334 A | 1/1995 | Torrier et al. |
| 5,445,833 A | 8/1995 | Badylak et al. |
| 5,447,940 A * | 9/1995 | Harvey et al. .............. 514/310 |
| 5,460,962 A | 10/1995 | Kemp |
| 5,464,929 A | 11/1995 | Bezwada et al. |
| 5,479,033 A | 12/1995 | Baca et al. |
| 5,514,181 A | 5/1996 | Light et al. |
| 5,516,533 A | 5/1996 | Badylak et al. |
| 5,520,691 A | 5/1996 | Branch |
| 5,545,178 A | 8/1996 | Kensey et al. |
| 5,554,389 A | 9/1996 | Badylak et al. |
| 5,569,252 A | 10/1996 | Justin et al. |
| 5,573,784 A | 11/1996 | Badylak et al. |
| 5,591,234 A | 1/1997 | Kirsch |

(Continued)

FOREIGN PATENT DOCUMENTS

EP          0 446 105 A2       1/1992

(Continued)

OTHER PUBLICATIONS

Definitions of "comminute" and "slurry". Dicitonary.com; accessed Sep. 20, 2005, 2 pages.*

Merriam-Webster Online Dictionary definitions of "suspension," "suspend," "cohesive," "cohesion," comminute," "pulverize," "submucosa," and "tissue." Accessed Mar. 30, 2006. 5 pages.*

Resin Technology Group, LLC. "Viscosity chart." http://www.resintechgroup.com/tables/viscosity.html, accessed online Mar. 30, 2006. 1 page.*

(Continued)

*Primary Examiner* — Lora E. Barnhart

(74) *Attorney, Agent, or Firm* — Barnes & Thornburg LLP

(57) ABSTRACT

Methods of making a hybrid biologic/synthetic scaffold for repairing damaged or diseased tissue are provided. The methods include the step of suspending pieces of an extracellular matrix material in a liquid to form a slurry, and coating a synthetic mat with the slurry, or mixing or layering the slurry with a synthetic polymer solution. The liquid is subsequently driven off so as to form a foam. Porous implantable scaffolds fabricated by such a method are also disclosed.

28 Claims, 3 Drawing Sheets

U.S. PATENT DOCUMENTS

| | | | |
|---|---|---|---|
| 5,593,441 A | 1/1997 | Lichtenstein et al. |
| 5,595,621 A | 1/1997 | Light et al. |
| 5,595,751 A | 1/1997 | Bezwada et al. |
| 5,597,579 A | 1/1997 | Bezwada et al. |
| 5,601,558 A | 2/1997 | Torrie et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,626,614 A | 5/1997 | Hart |
| 5,630,824 A | 5/1997 | Hart |
| 5,632,745 A | 5/1997 | Schwartz |
| 5,641,518 A | 6/1997 | Badylak et al. |
| 5,645,850 A | 7/1997 | Bezwada et al. |
| 5,645,860 A | 7/1997 | Knapp, Jr. et al. |
| 5,648,088 A | 7/1997 | Bezwada et al. |
| 5,660,225 A | 8/1997 | Saffran |
| 5,668,288 A | 9/1997 | Storey et al. |
| 5,669,912 A | 9/1997 | Spetzler |
| 5,677,355 A | 10/1997 | Shalaby et al. |
| 5,681,353 A | 10/1997 | Li et al. |
| 5,693,085 A | 12/1997 | Bulrge et al. |
| 5,695,998 A | 12/1997 | Badylak et al. |
| 5,698,213 A | 12/1997 | Jamiolkowski et al. |
| 5,700,583 A | 12/1997 | Jamiolkowski et al. |
| 5,702,462 A | 12/1997 | Oberlander |
| 5,711,969 A | 1/1998 | Patel et al. |
| 5,725,556 A | 3/1998 | Moser et al. |
| 5,730,933 A | 3/1998 | Peterson |
| 5,733,337 A | 3/1998 | Carr, Jr. et al. |
| 5,733,868 A | 3/1998 | Peterson et al. |
| 5,735,897 A | 4/1998 | Buirge |
| 5,735,903 A | 4/1998 | Li et al. |
| 5,736,372 A | 4/1998 | Vacanti et al. |
| 5,753,267 A | 5/1998 | Badylak et al. |
| 5,755,791 A | 5/1998 | Whitson et al. |
| 5,759,190 A | 6/1998 | Vibe-Hansen et al. |
| 5,759,205 A | 6/1998 | Valentini |
| 5,759,208 A | 6/1998 | Zhen et al. |
| 5,762,966 A | 6/1998 | Knapp et al. |
| 5,769,899 A | 6/1998 | Schwartz et al. |
| 5,773,577 A | 6/1998 | Cappello |
| 5,788,625 A | 8/1998 | Plouhar et al. |
| 5,795,353 A | 8/1998 | Felt |
| 5,800,537 A | 9/1998 | Bell |
| 5,830,708 A | 11/1998 | Naughton |
| 5,834,232 A | 11/1998 | Bishop et al. |
| 5,842,477 A | 12/1998 | Naughton et al. |
| 5,847,012 A | 12/1998 | Shalaby et al. |
| 5,855,610 A | 1/1999 | Vacanti et al. |
| 5,855,613 A | 1/1999 | Antanavich et al. |
| 5,855,619 A | 1/1999 | Caplan et al. |
| 5,859,150 A | 1/1999 | Jamiolkowski et al. |
| 5,861,004 A | 1/1999 | Kensey et al. |
| 5,863,551 A | 1/1999 | Woerly |
| 5,865,849 A | 2/1999 | Stone |
| 5,866,414 A | 2/1999 | Badylak et al. |
| 5,885,619 A | 3/1999 | Patel et al. |
| 5,891,558 A | 4/1999 | Bell et al. |
| 5,899,939 A | 5/1999 | Boyce et al. |
| 5,906,997 A | 5/1999 | Schwartz et al. |
| 5,916,265 A | 6/1999 | Hu |
| 5,922,028 A | 7/1999 | Plouhar et al. |
| 5,939,323 A | 8/1999 | Valentini et al. |
| 5,948,429 A | 9/1999 | Bell et al. |
| 5,954,723 A | 9/1999 | Spetzler |
| 5,954,747 A | 9/1999 | Clark |
| 5,955,110 A | 9/1999 | Patel et al. |
| 5,958,874 A | 9/1999 | Clark et al. |
| 5,968,096 A | 10/1999 | Whitson et al. |
| 5,969,020 A | 10/1999 | Shalaby et al. |
| 5,971,987 A | 10/1999 | Huxel et al. |
| 5,980,524 A | 11/1999 | Justin et al. |
| 5,981,802 A | 11/1999 | Katz |
| 5,981,825 A | 11/1999 | Brekke |
| 5,989,269 A | 11/1999 | Vibe-Hansen et al. |
| 5,989,280 A | 11/1999 | Euteneuer et al. |
| 5,993,475 A | 11/1999 | Lin et al. |
| 5,993,844 A | 11/1999 | Abraham et al. |
| 5,997,575 A | 12/1999 | Whitson et al. |
| 6,010,525 A | 1/2000 | Bonutti et al. |
| 6,017,301 A | 1/2000 | Schwartz et al. |
| 6,017,348 A | 1/2000 | Hart et al. |
| 6,027,744 A | 2/2000 | Vacanti et al. |
| 6,034,140 A | 3/2000 | Schwartz et al. |
| 6,042,610 A | 3/2000 | Li et al. |
| 6,051,750 A | 4/2000 | Bell |
| 6,056,752 A | 5/2000 | Roger |
| 6,056,777 A | 5/2000 | McDowell |
| 6,056,778 A | 5/2000 | Grafton et al. |
| 6,060,640 A | 5/2000 | Pauley et al. |
| 6,066,160 A | 5/2000 | Colvin et al. |
| 6,068,648 A | 5/2000 | Cole et al. |
| 6,077,989 A | 6/2000 | Kandel et al. |
| 6,080,194 A | 6/2000 | Pachence et al. |
| 6,093,201 A | 7/2000 | Cooper et al. |
| 6,096,347 A | 8/2000 | Geddes et al. |
| 6,099,567 A | 8/2000 | Badylak et al. |
| 6,110,212 A | 8/2000 | Gregory |
| 6,126,686 A | 10/2000 | Badylak et al. |
| 6,133,325 A | 10/2000 | Schwartz et al. |
| 6,146,385 A | 11/2000 | Torrie et al. |
| 6,152,935 A | 11/2000 | Kammerer et al. |
| 6,153,292 A | 11/2000 | Bell et al. |
| 6,156,044 A | 12/2000 | Kammerer et al. |
| 6,165,225 A | 12/2000 | Antanavich et al. |
| 6,171,344 B1 | 1/2001 | Atala |
| 6,176,880 B1 | 1/2001 | Plouhar et al. |
| 6,179,840 B1 | 1/2001 | Bowman |
| 6,179,872 B1 | 1/2001 | Bell et al. |
| 6,187,039 B1 | 2/2001 | Hiles et al. |
| 6,197,296 B1 | 3/2001 | Davies et al. |
| 6,206,931 B1 | 3/2001 | Cook et al. |
| 6,214,048 B1 | 4/2001 | Ito et al. |
| 6,214,049 B1 | 4/2001 | Gayer et al. |
| 6,224,892 B1 | 5/2001 | Searle |
| 6,235,057 B1 | 5/2001 | Roger et al. |
| 6,242,247 B1 | 6/2001 | Rieser et al. |
| 6,251,143 B1 | 6/2001 | Schwartz et al. |
| 6,251,876 B1 | 6/2001 | Bellini et al. |
| 6,258,124 B1 | 7/2001 | Darois et al. |
| 6,264,702 B1 | 7/2001 | Ory et al. |
| 6,265,333 B1 | 7/2001 | Dzenis et al. |
| 6,267,957 B1 | 7/2001 | Green et al. |
| 6,270,530 B1 | 8/2001 | Eldridge et al. |
| 6,273,893 B1 | 8/2001 | McAllen, III et al. |
| 6,280,473 B1 | 8/2001 | Lemperle et al. |
| 6,280,474 B1 | 8/2001 | Cassidy et al. |
| 6,283,980 B1 | 9/2001 | Vibe-Hansen et al. |
| 6,288,043 B1 | 9/2001 | Spiro et al. |
| 6,290,711 B1 | 9/2001 | Caspari et al. |
| 6,293,961 B2 | 9/2001 | Schwartz et al. |
| 6,294,041 B1 | 9/2001 | Boyce et al. |
| 6,299,905 B1 | 10/2001 | Peterson et al. |
| 6,306,156 B1 | 10/2001 | Clark |
| 6,306,159 B1 | 10/2001 | Schwartz et al. |
| 6,306,177 B1 | 10/2001 | Felt et al. |
| 6,319,258 B1 | 11/2001 | McAllen, III et al. |
| 6,319,271 B1 | 11/2001 | Schwartz et al. |
| 6,326,025 B1 | 12/2001 | Sigler et al. |
| 6,333,029 B1 | 12/2001 | Vyakarnam et al. |
| 6,334,872 B1 | 1/2002 | Termin et al. |
| 6,355,699 B1 | 3/2002 | Vyakarnam et al. |
| 6,358,284 B1 | 3/2002 | Fearnot et al. |
| 6,364,884 B1 | 4/2002 | Bowman et al. |
| 6,371,958 B1 | 4/2002 | Overaker |
| 6,373,221 B1 | 4/2002 | Koike et al. |
| 6,379,367 B1 | 4/2002 | Vibe-Hansen et al. |
| 6,379,710 B1 | 4/2002 | Badylak |
| 6,383,221 B1 | 5/2002 | Scarborough et al. |
| 6,387,693 B2 | 5/2002 | Rieser et al. |
| 6,402,766 B2 | 6/2002 | Bowman et al. |
| 6,409,764 B1 | 6/2002 | White et al. |
| 6,423,073 B2 | 7/2002 | Bowman |
| 6,436,110 B2 | 8/2002 | Bowman et al. |
| 6,440,444 B2 | 8/2002 | Boyce et al. |
| 6,447,517 B1 | 9/2002 | Bowman |
| 6,451,032 B1 | 9/2002 | Ory et al. |

| | | |
|---|---|---|
| 6,458,158 B1 | 10/2002 | Anderson et al. |
| 6,458,383 B2 | 10/2002 | Chen et al. |
| 6,464,729 B1 | 10/2002 | Kandel |
| 6,497,650 B1 | 12/2002 | Nicolo |
| 6,497,707 B1 | 12/2002 | Bowman et al. |
| 6,508,821 B1 | 1/2003 | Schwartz et al. |
| 6,517,564 B1 | 2/2003 | Grafton et al. |
| 6,566,345 B2 | 5/2003 | Miller et al. |
| 6,572,650 B1 | 6/2003 | Abraham et al. |
| 6,592,623 B1 | 7/2003 | Bowlin et al. |
| 6,638,312 B2 | 10/2003 | Plouhar et al. |
| 6,652,872 B2 | 11/2003 | Nevo et al. |
| 6,666,892 B2 | 12/2003 | Hiles et al. |
| 6,692,499 B2 | 2/2004 | Törmäläet et al. |
| 6,733,787 B2 | 5/2004 | Peterson et al. |
| 6,812,221 B2 | 11/2004 | McKeehan et al. |
| 6,840,962 B1 | 1/2005 | Vacanti et al. |
| 6,869,938 B1 | 3/2005 | Schwartz et al. |
| 6,989,034 B2 | 1/2006 | Hammer et al. |
| 2001/0002446 A1 | 5/2001 | Plouhar et al. |
| 2001/0023373 A1 | 9/2001 | Plouhar et al. |
| 2001/0024658 A1 | 9/2001 | Chen et al. |
| 2001/0043943 A1 | 11/2001 | Coffey |
| 2002/0019649 A1 | 2/2002 | Sikora et al. |
| 2002/0031551 A1 | 3/2002 | Peterson et al. |
| 2002/0038151 A1 | 3/2002 | Plouhar et al. |
| 2002/0048595 A1 | 4/2002 | Geistlich et al. |
| 2002/0099448 A1 | 7/2002 | Hiles |
| 2002/0173806 A1 | 11/2002 | Giannetti et al. |
| 2003/0014126 A1 | 1/2003 | Patel et al. |
| 2003/0021827 A1 | 1/2003 | Malaviya et al. |
| 2003/0023316 A1 | 1/2003 | Brown et al. |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0044444 A1 | 3/2003 | Malaviya et al. |
| 2003/0049299 A1 | 3/2003 | Malaviya et al. |
| 2003/0212447 A1 | 11/2003 | Euteneuer et al. |
| 2004/0143344 A1 | 7/2004 | Malaviya et al. |

FOREIGN PATENT DOCUMENTS

| | | |
|---|---|---|
| EP | 0591991 A2 | 4/1994 |
| EP | 0632999 A1 | 11/1995 |
| EP | 0 734 736 A1 | 10/1996 |
| EP | 1593400 A1 | 11/2005 |
| FR | 2422386 | 4/1978 |
| GB | 2 215 209 | 9/1989 |
| JP | 11319068 A | 11/1999 |
| WO | WO 90/09769 | 9/1990 |
| WO | 9403584 | 2/1994 |
| WO | WO 94/11008 | 5/1994 |
| WO | WO 95/05083 | 2/1995 |
| WO | WO 95/22301 | 8/1995 |
| WO | WO 95/06439 | 9/1995 |
| WO | 9532623 | 12/1995 |
| WO | WO 95/32623 | 12/1995 |
| WO | 9625961 | 8/1996 |
| WO | WO 96/24661 | 8/1996 |
| WO | WO 97/05193 | 2/1997 |
| WO | 9715195 | 5/1997 |
| WO | 9730662 | 8/1997 |
| WO | WO 97/37613 | 10/1997 |
| WO | WO 98/06445 | 2/1998 |
| WO | 9822154 | 5/1998 |
| WO | WO 98/22158 A2 | 5/1998 |
| WO | WO 98/22158 A3 | 5/1998 |
| WO | WO 98/30167 | 7/1998 |
| WO | WO 98/34569 | 8/1998 |
| WO | WO 98/40111 | 9/1998 |
| WO | WO 99/03979 | 1/1999 |
| WO | 9919005 | 4/1999 |
| WO | WO 99/43786 | 9/1999 |
| WO | WO 99/47188 | 9/1999 |
| WO | 0015153 | 3/2000 |
| WO | WO 00/15765 | 3/2000 |
| WO | WO 00/16822 | 3/2000 |
| WO | WO 00/24437 A2 | 5/2000 |
| WO | WO 00/24437 A3 | 5/2000 |
| WO | WO 00/32250 | 6/2000 |
| WO | WO 00/48550 | 8/2000 |
| WO | 0072782 | 12/2000 |
| WO | WO 00/72782 | 12/2000 |
| WO | WO 01/19423 | 3/2001 |
| WO | WO 01/39694 A2 | 6/2001 |
| WO | WO 01/39694 A3 | 6/2001 |
| WO | WO 01/45765 | 6/2001 |
| WO | WO 01/66159 | 9/2001 |
| WO | WO 01/70293 A1 | 9/2001 |
| WO | WO 02/22184 | 3/2002 |
| WO | WO 03/007784 | 1/2003 |
| WO | WO 03/007788 A2 | 1/2003 |
| WO | WO 03/007790 A2 | 1/2003 |

OTHER PUBLICATIONS

Definitions of "intertwine" and "twine." American Heritage Dicitonary of the English Language Online. Accessed Sep. 29, 2005. 2 pages.*
Hiles et al., "Mechanical properties of xenogeneic small-intestinal submucosa when used as an aortic graft in the dog", *Journal of Biomedical Materials Research*, vol. 29, 883-891, (1995).
Sandusky, et al., "Healing Comparison of Small Intestine Submucosa and ePTFE Grafts in the Canine Carotid Artery", *J. Surg. Res.*, 58:415-420, (1995).
Knapp, et al., "Biocompatibility of Small-Intestine Submucosa in Urinary Tract as Augmentation Cystoplasty Graft and Injectable Suspension", *J Endourology*, 8:125-130, (1994).
Kropp et al., "Regenerative Bladder Augmentation: A Review of the Initial Preclinical Studies with Porcine Small Intestinal Submucosa", *Muscle, Matrix, and Bladder Function*, Plenum Press, New York, (1995).
Kropp et al., "Experimental Assessment of Small Intestinal Submucosa as a Bladder Wall Substitute", *Urology* 446:396-400, (1995).
Vaught et al., "Detrusor Regeneration in the Rat Using Porcine Small Intestinal Submucosa Grafts: Functional Innervation and Receptor Expression", *J. Urol.*, 155:374-378, (1996).
Kropp et al, Characterization of Small Intestinal Submucosa Regenerated Canine Detrusor: Assessment of Reinervation, In Vitro Compliance and contractility. *J. of Urol.*, 156:599-607, (1996).
Kropp et al., "Regenerative Urinary Bladder Augmentation Using Small Intestinal Submucosa: Urodynamic and Histopathologic Assessment in Long-Term Canine Bladder Augmentations", *Journal of Urology*, 155:2098-2104, (1996).
Aiken et al., "Small Intestinal Submucosa as an Intra-Articular Ligamentous Graft Material: A Pilot Study in Dogs", *Vet Comp Orthopedics Traumatology*, 7:124-128, (1994).
Badylak et al., "The Use of Xenogeneic Small Intestinal Submucosa as a Biomaterial for Achille's Tendon Repair in a dog model", *J. Biomed. Materials*, 29:977-985 (1995).
Hodde et al., "The Effect of Range of Motion Upon Remodeling of Small Intestinal Submucosa (SIS) when used as an Achilles Tendon Repair Material in the Rabbit", *Tissue Engineering 3*, 1:27-37, (1997).
Ferrand et al., "Directional Porosity of Porcine Small-Intestinal Submucosa", *J Biomed Materials Res*, 27:1235-1241, (1993).
Hiles et al., "Porosity of Porcine Small-Intestinal Submucosa for use as a Vascular Graft", *J Biomed Materials Res*, 27: 139-144. (1993).
Hodde et al., "Glycosminoglycan Content of Small Intestinal Submucosa: A Bioscaffold for Tissue Replacement", *Tissue Engineering*, 2:3, 209-217, (1996).
Prevel et al., "Small Intestinal Submucosa: Utilization for Repair of Rodent Abdominal Wall Defects", *Ann Plast Surg*, 35:374-380, (1995).
Clarke et al., "Intestine Submucosa and Polypropylene Mesh for Abdominal Wall Repair in Dogs", *J Surg Res*, 60:107-114, (1996).
Prevel et al., "Small Intestinal Submucosa: Utilization as a Wound Dressing in Full-Thickness Rodent Wounds", *Ann Plast Surg*, 35:381-388, (1995).
Cobb et al., "Histology after Dural Grafting with Small Intestinal Submucosa", *Surgical Neurology*, 46: 389-394, (1994).

Cobb et al., "Porcine Small Intestinal Submucosa as a Dural Substitute", *Surgical Neurology*, 51:99-1-4, (1999).
Voytik-Harbin et al., "Application and Evaluation of the AlamarBlue Assay for Cell Growth and Survival of Fibroblasts", *Journal of Immunological Methods, In Vitro Cell Bio-Animal*, 34: 2399-246, (1998).
Suckow, M.A., "Enhanced Bone Regeneration Using Porcine Small Intestinal Submucosa", *J. Invest Surg*, 12: 277, (1999).
Badylak, S., et al., "Naturally Occurring Extracellular Matrix as a Scaffold for Musculoskeletal Repair", *Clin Orthop*, 3675:S333-S3433, (1999).
Cook, J.L. et al., "Induction of Meniscal Regeneration in Dogs Using a Novel Biomaterial", *Am J Sports Med*, 27: 658, (1999).
Dejardin, L.M. et al., "Use of small intestinal submucosal implants for regeneration of large fascial defects: an experimental study in dogs", *J Biomed Mater Res*, 46:203-211, (1999).
Sacks, M.S., et al., "Quantification of the fiber architecture and biaxial mechanical behavior of porcine intestinal submucosa", *J Biomed Mater Res*, 46:1-10, (1999).
COOK® News Releases, "COOK® Introduces Innovative Surgisis™ Soft Tissue Repair Biomaterial", (May 21, 2000).
COOK® News Releases, "COOK® Oasis™ Wound Dressing Biomaterial From COOK® Remodels Partial Thickness Skin Injuries", (Dec. 23, 1999).
COOK® News Releases, "Cook Incorporated Forms Dedicated Tissue Engineered Products Group", (Feb. 16, 2000).
COOK® News Releases, "FDA Clears Oasis™ Wound Dressing Biomaterial From COOK® for Full-Thickness Skin Injuries", (Jan. 24, 2000).
Klootwyk, et al., "The Use of Xenographic SIS as a Biomaterial for Achilles Tendon Repair in Dogs," First SIS Symposium, Dec. 1996, USA.
Lenz, et al., "SIS as an ACL Replacement in Dogs and Goats," First Symposium, Dec. 1996, USA.
Cook, et al., "Comparison of SIS Cancellous Bone as Substrates for Three-Dimensional Culture of Canine Articular Chondrocytes," First SIS Symposium, Dec. 1996, USA.
Badylak, et al., "Different Configurations of Small Intestinal Submucosa as a Biomaterial for Achilles Tendon Repair in a Dog Model," First SIS Symposium, Dec. 1996, USA.
Voytik-Harbin & Badylak, "Induction of Osteogenic Activity by Small Intestinal Submucosa in Rat Calvaria Non-union Defects," First SIS Symposium, Dec. 1996, USA.
Kandel, et al., "SIS and Reconstituted Cartilage and Its Use in Joint Resurfacing of Focal Defects in Rabbits," First SIS Symposium, Dec. 1996, USA.
Tullius, et al., "Differential Permeabilty of SIS," First SIS Symposium, Dec. 1996, USA.
Obermiller, et at., "Suture Retention Strength of SIS," First SIS Symposium, Dec. 1996, USA.
Shelton, et al., "Repair of the Canine Medial Meniscus using SIS: A Feasibility Study," Second SIS Symposium, Dec. 1998, USA.
Cook, et al., "Meniscal Regeneration in dogs Using Grafts of SIS," Second SIS Symposium, Dec. 1998, USA.
Welch, et al., "Healing of Canine Meniscal Defect with Small Intestinal Submucosa Implants," Dec. 1998, USA.
Solchaga, et al., "SIS as Delivery Vehicle for Mesenchymal Progenitor Cells," Dec. 1998, USA.
Paulino, et al., "The Use of an SIS-PGA Composite Graft for Repair of Cartilage Defect," Dec. 1998, USA.
Toombs and May, "Clinical Follow-Up of Three Canine ACL Reconstructions Using an SIS ACL Device," Dec. 1998, USA.
Tomasek and Gifford, "Small Intestinal Submucosa Matrix Regulates the Differentiation of Myofibroblasts," Third SIS Symposium, Nov. 2000, USA.
Cook, et al., "Tissue Engineering for Meniscal Repair Using SIS," Third SIS Symposium, Nov. 2000, USA.
Lifrak, et al., "Enhanced Repair of Goat Meniscal Defects Using Porcine Small Intestinal Submucosa (SIS)," Third SIS Symposium, Nov. 2000, USA.
Hoffman, "SIS Disc Replacement for the Temporomandibular Joint," Third SIS Symposium, Nov. 2000, USA.
Kaeding, "Use of SIS in the Surgical Treatment of Chronic Symptomatic Patella Tendinosis," Third SIS Symposium, Nov. 2000, USA.
Tomczak and Kaeding, "Use of SIS in the Surgical Treatment of Tendinosis About The Foot and Ankle," Third SIS Symposium, Nov. 2000, USA.
Moore, et al., "Bridging Segmental Defects In Long Bones With Intramedullary Tubes And Periosteal Sleeves Made From Small Intestinal Submucosa (SIS)," Third SIS Symposium, Nov. 2000, USA.
Wang, et al., "Small Intestinal Submucosa Enhances Healing of Medical Collateral Ligament In A Rabbit Model," Third SIS Symposium, Nov. 2000, USA.
Ojha, et al., "PGA-PIIA Versus Small Intestinal Submucosa (SIS): A Comparison of Neo-Cartilage Grown From Two Scaffold Materials," Third SIS Symposium, Nov. 2000, USA.
Wiklerson, "Use of the Porcine Small Intestine Submucosal Tissue Graft And Repair of Rotator Cuff Tears," Third SIS Symposium, Nov. 2000, USA.
"Small Intestinal Submucosa," Third SIS Symposium, Nov. 2000, USA.
"Current Clinical Applications of SIS" Third SIS Symposium, Nov. 2000, USA.
Hodde, et al., "Glycosaminoglycan Content of Small Intestinal Submucosa: A Potential for GAG-Growth Interactions in SIS-Mediated Healing", First Symposium, Dec. 1996, USA.
Friess, "Collagen in drug delivery and tissue engineering", *Advanced Drug Delivery Reviews*, vol. 55, No. 12, 2003, pp. 1529-1530.
Olsen et al., "Recombinant collagen and gelatin for drug delivery", *Advanced Drug Delivery Reviews*, vol. 55, No. 12, 2003, pp. 1547-1567.
Aigner et al., "Collagens-major component of the physiological cartilage matrix, major target of cartilage degeneration, major tool in cartilage repair", *Advanced Drug Delivery Reviews*, vol. 55, No. 12, 2003, pp. 1569-1593.
Geiger et al., "Collagen sponges for bone regeneration with rhBMP-2", *Advanced Drug Delivery Reviews*, vol. 55, No. 12, 2003, pp. 1613-1629.
Ruszczak et al., "Collagen as a carrier for on-site delivery of antibacterial drugs", *Advanced Drug Delivery Reviews*, vol. 55, No. 12, 2003, pp. 1679-1698.
O'Grady et al., "Global regulatory registration requirements for collagen-based combination products: points to consider", *Advanced Drug Delivery Reviews*, vol. 55, No. 12, 2003, pp. 1699-1721.
Matthews et al., "Electrospinning of Collagen Type II: A Feasibility Study", *Journal of Bioactive and Compatible Polymers*, vol. 18, Mar. 2003, pp. 125-134.
Biscarini et al., "Growth of High Vacuum Sublimed Oligomer Thin Films", *ACS Polymer Preprints*, vol. 37, No. 1996, pp. 618-619.
Biscarini et al., "Morphology and roughness of high-vacuum sublimed oligomer thin films", *Thin Solid Films*, vol. 439-443, 1996, pp. 284-285.
Biscarini et al., "Scaling Behavior of Anisotropic Organic Thin Films Grown in High-Vacuum", *Physical Review Letters*, vol. 78, No. 12, Mar. 24, 1997, pp. 2389-2392.
Voytik-Harbin et al., "Identification of Extractable Growth Factors from Small Intestinal Submucosa", *Journal of Cellular Biochemistry*, vol. 67, 1997, pp. 478-491.
McPherson, Ph.D. et al., "Characterization of Fibronectin Derived from Porcine Small Intestinal Submucosa", *Tissue Engineering*, vol. 4, No. 1, 1998, pp. 75-83.
Hodde, et al., "Vascular Endothelial Growth Factor in Porcine-Derived Extracellular Matrix", *Endothelium*, vol. 8(1), 2001, pp. 11-24.
Hodde et al., "Wounds: A Compendium of Clinical Research and Practice", *Website*: http:www.hmpcommunications.com/WNDS, Printed: Jul. 12, 2005, 7 pgs.
Hurst et al., "Mapping of the distribution of significant proteins and proteoglycans in small intestinal submucosa by fluorescence microscopy", *J. Biomater. Sci. Polymer Edn.*, vol. 12, No. 11, 2001, pp. 1267-1279.
Hodde et al., "Fibronectin peptides mediate HMEC adhesion to porcine-derived extracellular matrix", *Biomaterials*, vol. 23, 2002, pp. 1841-1848.

Hodde, "Naturally Occurring Scaffolds for Soft Tissue Repair and Regeneration", *Tissue Engineering*, vol. 8, No. 2, 2002, pp. 295-308.

Allman et al., Xenogeneic Extracellular Matrix Grafts Elicit a Th2-Restricted Immune Response, *Transplantation*, vol. 71, No. 11, Jun. 15, 2001, pp. 1631-1640.

Allman et al., "The Th2-Restricted Immune Response to Xenogeneic Small Intestinal Submucosa Does Not Influence Systemic Protective Immunity to Viral and Bacterial Pathogens", *Tissue Engineering*, vol. 8, No. 1, 2002, pp. 53-62.

Krčma, "Nonwoven Textiles", *Textile Trade Press, Manchester, England*, 1962, 6 pgs.

Answers.com,. Definition of "freeze-dry", Accessed on May 12, 2005, 6 pgs.

Ma et al., "Microtubular architecture of biodegradable polymer scaffolds", *J. Biomed. Materials Res.*, vol. 56, No. 4, 2001, pp. 469-477.

Ma et al., "Biodegradable Polymer Scaffolds with Well-Defined Interconnected Spherical Pore Network", *Tissue Engineering*, vol. 7, No. 1, 2001, pp. 23-33.

Klawitter et al., "An Evaluation of Bone Growth into Porous High Density Polyethylene", *J. Biomed. Materials Res.*, vol. 10, (1976) pp. 311-323.

Shors, Coralline Bone Graft Substitutes, *Orthopaedic Clinics of North America*, Bone Grafting and Bone Graft Substitutes, vol. 30, No. 4, Oct. 1999, pp. 599-613.

Wang, Experimental Study of Osteogenic Activity of Sintered Hydroxyapatite—On the Relationship of Sintering Temperature and Pore Size—, *J. Jpn. Orthop. Assoc.*, vol. 64, 1990, pp. 847-859.

Nehrer et al., "Matrix collagen type and pore size influence behavior of seeded canine chondrocytes", *Biomaterials*, vol. 18, No. 11, 1997, pp. 769-776.

Salem et al., "Interactions of 3T3 fibroblasts and endothelial with defined pore ffeatures", *J. Biomed Materials Res.*, vol. 61, No. 2, 2002, pp. 212-217.

P. K. Chu et al., "Plasma-surface modification of biomaterials", Materials Science and Engineering, Reports: A Review Journal, vol. 36, No. 5-6, Mar. 29, 2002, pp. 143-206.

Arnoczky at al., The microvasculature of the meniscus and its response to injury—An experimental study in the dog, *Am. J. Sports Med.*, 1983, 11(3); pp. 131-141.

Fox et al., Trephination of incomplete meniscal tears, *Arthroscopy*, 1993, 9(4); pp. 451-5.

Arnoczky et al., Meniscal repair using an exogenous fibrin clot—An experimental study of dogs, *J. Bone Joint Surg. Am.*, 1988, 70(8), pp. 1209-1216.

Rodeo, "Arthroscopic meniscal repair with use of the outside-in technique", *Instr. Course Lect.*, 2000, 49, pp. 195-206.

Stollsteimer et al., "Meniscal allograft transplantation: a 1- to 5-year follow-up of 22 patients", *Arhroscopy*, 2000, 18(4), pp. 343-7.

Rodeo, "Meniscal allografts—where do we stand?", *Am. J. Sports Med.*, 2001, 29(2), pp. 246-61.

Sweigart et al., "Toward tissue engineering of the knee meniscus", *Tissue Eng.*, 2001, 7(2), pp. 111-129.

Boss at al., "Technical innovative: creation of a peripheral vascularized trough to enhance healing in cyropreserved meniscal allograft reconstruction", *Knee Surg Sports Traumatol Arthrosc.*, 2000, 8(3), pgs.

Siegel et al., "Meniscal allografts", *Clin Sports Med.*, 1993, 12(1), pp. 59-80.

Klompmaker et al., "Meniscal replacement using a porous polymer prosthesis: a preliminary study in the dog.", *Biomaterials*, 1996, 17(12), pp. 1169-1175.

de Groot et al., "Use of porous polyurethanes for meniscal reconstruction and meniscal protheses", *Biomaterials*,1996, 17(2), pp. 163-73.

Spaans et al., "Solvent-free fabrication of micro-porous polyurethane amide and polyurethane-urea scaffolds for repair and replacement of the knee-joint meniscus", *Biomaterials*, 2000, 21(23), pp. 2453-2460.

Stone et al., "Regeneration of meniscal cartilage with use of a collagen scaffold—Analysis of Preliminary data", *J. Bone Joint Surg. Am.*, 1997, 79(12), pp. 1770-1777.

Rodkey et al., "A clinical study of collagen meniscus implants to restore the injured meniscus", *Clin. Orthop.*, 1999, 49(367 Suppl.), pp. s281-s292.

J.S. Pieper et al "Preparation and characterization of porous crosslinked collagenous matrices containing bioavailable chondroitin suplhate" *Biomaterials* 1999, 20: 847-858.

P.B. van Wachem et al. "In vivo biocompatability of carbodiimide-crosslinked collagen matrices: Effects of crosslink density, heparin immobilization, and bFGF loading" J. Biomed. Mater. Res. 2001, 55 (3): 368-378.

Kyumin Whang "A biodegradable polymer scaffold for delivery of osteotropic factors" Biomaterials 2000, 21 (24): 2545-2551.

J.S. Pieper et al. Attachment of glycosaminoglycans to collangenous matrices modulates the tissue response in rats, Biomaterials 2000, 21 (16): 1689-1699.

Kristen Billiar et al. "Effects of carbodiimide crosslinking conditions on the physical properties of laminated intestinal submucosa", J. Biomed. Mater. Res. 2001, 51(1): 101-108.

Toshimitsu Momose et al. "Surface modification of extrasynovial tendon by chemically modified hyaluronlc acid coating" J. Biomed. Mater. Res. 2002, 59: 219-224.

Handbook of Biodegradable Polymers Hardwood Press 1997 (251-272).

Cohn et al., "Biodegradable PEO/PLA block copolymers," Journal of Biomedical Materials Research, 1988, 22 (993-1009).

"Polymer Preprints" (ACS Division of Polymer Chemistry), 1989, 30 (1): 498.

The Encyclopedia of Polymer Science, 1988 (13) 31-41.

"Handbook of Biodegradable Polymers" Hardwood Press 1977 (161-182).

"Handbook of Biodegradable Polymers" Hardwood Press 1997 (99-118).

Disilvestro et al., "Effects of Cross-Linking on the Mechanical Properties of a Porous Foam Scaffold of Small Intestine Submucosa", Society for Biomaterials 29th Annual Meeting Transactions, 2003, pp. 88.

Ide et al., "Collagen Hybridization with Poly(I-Lactic Acid) Braid Promotes Ligament Cell Migration", Mater. Sci. Eng. C, 17(1-2), 95-99 (2001).

Bercovy et al., "Carbon-PGLA Prosthesis for Ligament Reconstruction Experimental Basis and Short Term Results in Man", Clin. Orthop. Relat. Res., (196), 159-68 (1985).

Zhu et al, "Immobilization of Biomacromolecules onto Aminolyzed Poly(L-lactic acid) toward Acceleration of Endothelium Regeneration", Tissue Engineering. v 10, pp. 53-61, 2004.

Cheng & Teoh, "Surface modification of ultra thin poly (ÿ caprolactone) films using acrylic acid and collagen", Biomaterials, v25(11), pp. 1991-2001, 2004.

Wan et al., "Cell adhesion on gaseous plasma modified poly-(L-lactide) surface under shear stress field", Biomaterials, v24(21), pp. 3757-3764, 2003.

Yang et al., "Effect of surface treatment on the biocompatibility of microbial polyhydroxyalkanoates", Biomaterials, v 23 (5), pp: 1391-1397, 2002.

Croll et al., "Controllable surface modification of Poly(lactic-co-glycolic acid) (PLGA) by hydrolysis or aminolysis I: physical, chemical, and theoretical aspects", Biomacromolecules, Mar.-Apr. 2004, 5(2): 463-473.

Kwon et al., "Fibroblast culture on surface-modified poly (glycolide-co- ÿ-caprolactone) scaffold for soft tissue regeneration", J. Biomater Sci Polym ed. 2001, 12(10) 1147-60.

Gastel JA, Muirhead WR, Lifrak JT, Fadale PD, Hulstyn MJ, Labrador DP "Meniscal tissue regeneration using a collagenous biomaterial derived from porcine small intestine submucosa", Arthroscopy, Feb; 17(2): 151-159.

Tan W, Krishnaraj R, Desai TA "Evaluation of nanostructured composite collagen-chitosan matrices for tissue engineering", Tissue Eng Apr; 7(2): 203-210, 2001.

Arnoczky SP "Building a meniscus", Biological considerations, Clin Orthop Oct; 367 (suppl), S244-53, 1999.

Metcalf et al., "Surgical technique for xenograft (SIS) augmentation of rotator-cuff repairs", Op Tech Orthop, 12(3): 204-208, 2002.

Courtney et al., "Modification of polymer surfaces: optimization of approaches", Perfusion, v 18 (11), pp. 33-39, 2003.

Zhang et al., Design of nanostructured biological materials through self-assembly of peptides and proteins, MIT Current Opinion in chemical Biology, 2002, 6:865-871.

Hodde and Hiles, "Bioactive FGF-2 in sterilized extracellular matrix", Wounds, 13(5): 195-201 (2001).

O'Meara, Patrick, "The basic science of meniscus repair," Orthopaedic review, Jun. 1993, pp. 681-686.

Schmitt et al., "Electron Microscope Investigations of the Structure of Collagen", J. Cellular Comp. Physiol., 20:11, 1942.

United States Patent & Trademark Office, Decision on Appeal, Appeal 2006-1953, Decided May 21, 2007.

European Search Report for European Application No. 02752290.3-1219, Mar. 26, 2007, 5 pages.

"Urschel Laboratories, Inc.—Comitrol Processor Model 1700", http://www.urschel.com/Comitrol_Processor_Model_1700_df.html, printed Jul. 9, 2008, 2 pages.

European Search Report for European Patent Application 02747019.4—1219, Mar. 16, 2007, 4 pgs.

European Search Report for European Patent Application 02752339.8—1219, Jul. 20, 2007, 5 pgs.

Definitions of "intertwine" and "twine", *American Heritage Dicitonary of the English Language Online*, Accessed Sep. 29, 2005, 2 pgs.

How to Cut Meat Products 2001, *Urschel Corp.*, Accessed online at fr.urschel.com/literature/HTCMeat.pdf on Oct. 3, 2005, 8 pgs.

Definitions of "comminute" and "slurry", *Dictionary.com*; Accessed Sep. 20, 2005, 2 pgs.

* cited by examiner

HYBRID BIOLOGIC/SYNTHETIC POROUS EXTRACELLULAR MATRIX SCAFFOLDS

This application claims priority to U.S. Patent Application No. 60/388,711, filed Jun. 14, 2002, and U.S. Provisional Application No. 60/305,786, filed Jul. 16, 2001, hereby incorporated by reference.

Cross reference is made to copending U.S. patent application Ser. No. 10/195,795 entitled "Meniscus Regeneration Device and Method", DEP-745); Ser. No. 10/195,719 entitled "Devices from Naturally Occurring Biologically Derived Materials"; Ser. No. 10/195,347 entitled "Cartilage Repair Apparatus and Method"; Ser. No. 10/195,344 entitled "Unitary Surgical Device and Method"; Ser. No. 10/195,606 entitled "Cartilage Repair and Regeneration Device and Method"; Ser. No. 10/195,354 entitled "Porous Extracellular Matrix Scaffold and Method"; Ser. No. 10/195,334 entitled "Cartilage Repair and Regeneration Scaffolds and Method"; and Ser. No. 10/195,633 entitled "Porous Delivery Scaffold and Method", each of which is assigned to the same assignee as the present application, each of which is filed concurrently herewith, and each of which is hereby incorporated by reference. Cross reference is also made to U.S. patent application Ser. No. 10/172,347 entitled "Hybrid Biologic-Synthetic Bioabsorbable Scaffolds" which was filed on Jun. 14, 2002, which is assigned to the same assignee as the present application, and which is hereby incorporated by reference.

TECHNICAL FIELD OF THE DISCLOSURE

The present disclosure relates generally to an extracellular matrix, scaffold, and more particularly to a porous extracellular matrix scaffold for repairing or regenerating body tissue and a method for making such a scaffold.

BACKGROUND AND SUMMARY

Naturally occurring extracellular matrices (ECMs) are used for tissue repair and regeneration. One such ECM is small intestine submucosa (SIS). SIS has been used to repair, support, and stabilize a wide variety of anatomical defects and traumatic injuries. Commercially-available SIS material is derived from porcine small intestinal submucosa that remodels the qualities of its host when implanted in human soft tissues. Further, it is taught that the SIS material provides a natural matrix with a three-dimensional microstructure and biochemical composition that facilitates host cell proliferation and supports tissue remodeling. SIS products, such as Oasis material and Surgisis material, are commercially available from Cook Biotech, Bloomington, Ind.

An SIS product referred to as RESTORE™ Orthobiologic Implant is available from DePuy Orthopaedics, Inc. in Warsaw, Ind. The DePuy product is described for use during rotator cuff surgery, and is provided as a resorbable framework that allows the rotator cuff tendon to regenerate itself. The RESTORE™ Implant is derived from porcine small intestine submucosa that has been cleaned, disinfected, and sterilized. Small intestine submucosa (SIS) has been described as a naturally-occurring ECM composed primarily of collagenous proteins. Other biological molecules, such as growth factors, glycosaminoglycans, etc., have also been identified in SIS. See Hodde et al., Tissue Eng. 2(3): 209-217 (1996); Voytik-Harbin et al., J. Cell Biochem., 67:478-491 (1997); McPherson and Badylak, Tissue Eng., 4(1): 75-83 (1998); Hodde et al., Endothelium, 8(1):11-24 (2001); Hodde and Hiles, Wounds, 13(5): 195-201 (2001); Hurst and Bonner, J. Biomater. Sci. Polym. Ed., 12(11) 1267-1279 (2001); Hodde et al., Biomaterial, 23(8): 1841-1848 (2002); and Hodde, Tissue Eng., 8(2): 295-308 (2002), all of which are incorporated by reference herein. During seven years of pre-clinical testing in animals, there were no incidences of infection transmission form the implant to the host, and the RESTORE™ Implant has not decreased the systemic activity of the immune system. See Allman et al., Transplant, 17(11): 1631-1640 (2001); Allman et al., Tissue Eng., 8(1): 53-62 (2002).

While small intestine submucosa is available, other sources of submucosa are known to be effective for tissue remodeling. These sources include, but are not limited to, stomach, bladder, alimentary, respiratory, or genital submucosa, or liver basement membrane. See, e.g., U.S. Pat. Nos. 6,379,710, 6,171,344, 6,099,567, and 5,554,389, hereby incorporated by reference. Further, while SIS is most often porcine derived, it is known that these various submucosa materials may be derived from non-porcine sources, including bovine and ovine sources. Additionally, the ECM material may also include partial layers of laminar muscularis mucosa, muscularis mucosa, lamina propria, stratum compactum and/or other tissue materials depending upon factors such as the source from which the ECM material was derived and the delamination procedure.

For the purposes of this invention, it is within the definition of a naturally occurring ECM to clean, delaminate, and/or comminute the ECM, or even to cross-link the collagen fibers within the ECM. It is also within the definition of naturally occurring ECM to fully or partially remove one or more sub-components of the naturally occurring ECM. However, it is not within the definition of a naturally occurring ECM to separate and purify the natural collagen or other components or sub-components of the ECM and reform a matrix material from the purified natural collagen or other components or sub-components of the ECM. While reference is made to SIS, it is understood that other naturally occurring ECMs (e.g., stomach, bladder, alimentary, respiratory, and genital submucosa, and liver basement membrane), whatever the source (e.g., bovine, porcine, ovine) are within the scope of this disclosure. Thus, in this application, the terms "naturally occurring extracellular matrix" or "naturally occurring ECM" are intended to refer to extracellular matrix material that has been cleaned, disinfected, sterilized, and optionally cross-linked. The terms "naturally occurring extracellular matrix" and "naturally occurring ECM" are also intended to include ECM foam material prepared as described in copending U.S. patent application Ser. No. 10/195,354 entitled "Porous Extracellular Matrix Scaffold and Method", filed concurrently herewith.

The following patents, hereby incorporated by reference, disclose the use of ECMs for the regeneration and repair of various tissues: U.S. Pat. Nos. 6,187,039; 6,176,880; 6,126,686; 6,099,567; 6,096,347; 5,997,575; 5,968,096; 5,955,110; 5,922,028; 5,885,619; 5,788,625; 5,762,966; 5,755,791; 5,753,267; 5,711,969; 5,645,860; 5,641,518; 5,554,389; 5,516,533; 5,445,833; 5,372,821; 5,352,463; 5,281,422; and 5,275,826.

The manipulation of scaffold pore size, porosity, and interconnectivity is of emerging importance in the field of tissue engineering (Ma and Zhang, 2001, J. Biomed Mater Res. 56(4): 469-477; Ma and Choi, 2001, Tissue Eng., 7(1):23-33), because it is believed that the consideration of scaffold pore size and density/porosity influences the behavior of cells and the quality of tissue regenerated. In fact, several researchers have shown that different pore sizes influence the behavior of cells in porous three-dimensional matrices. For example, it has been demonstrated in the art that for adequate bone regeneration to occur scaffold pore size should to be at least 100 microns (Klawitter et al., 1976, J Biomed Mater Res, 10(2): 311-323). For pore sizes and interconnectivity less than that, poor quality bone is regenerated, and if pore size is between 10-40 microns bone cells are able to form only soft fibro-vascular tissue (White and Shors, 1991, Dent Clin North Am, 30:49-67). The current consensus of research for bone regeneration indicates that the requisite pore size for bone regeneration is 100-600 microns (Shors, 1999, Orthop Clin North Am, 30(4):599-613; Wang, 1990, Nippon Seikeigeka Gakki Zasshi, 64(9):847-859). It is generally accepted that optimal bone regeneration occurs for pore sizes between 300-600 microns.

Similarly, for the regeneration of soft orthopaedic tissues, such as ligament, tendon, cartilage, and fibro-cartilage, scaffold pore size is believed to have a substantial effect. For example, basic research has shown that cartilage cells (chondrocytes) exhibit appropriate protein expression (type II collagen) in scaffolds with pore sizes of the order of 20 microns and tend to dedifferentiate to produce type I collagen in scaffolds with nominal porosity of about 80 microns (Nehrer et al., 1997, Biomaterials, 18(11):769-776). More recently, it has been shown that cells that form ligaments, tendons, and blood vessels (fibroblasts and endothelial cells) exhibit significantly different activity when cultured on scaffolds with differing pore sizes ranging from 5 to 90 microns (Salem et al., 2002, J Biomed Mater Res, 61(2):212-217).

Copending U.S. application Ser. No. 10/195,354 entitled "Porous Extracellular Matrix Scaffold and Method", DEP-747), filed contemporaneously herewith and hereby incorporated by reference, describes methods for making ECM foams wherein the porosity is controlled. Using the methods so described, ECM foams are made having the desired porosity for a particular application.

In some applications, it is also desirable to control the rate of resorption of the scaffold. It is known in the art to make implantable three-dimensional synthetic scaffolds with controlled porosity and controlled resorption rates. See, e.g., U.S. Pat. Nos. 6,333,029 and 6,355,699, hereby incorporated by reference. These synthetic foams may be isotropic in form, or may be anisotropic, providing various gradient architectures.

In addition to synthetic foams, it is known that resorption rates of an implant may be controlled by providing a synthetic portion comprising a perforated or non-perforated sheet or a mat with a woven, knitted, warped knitted (i.e., lace-like), nonwoven, or braided structure. It is understood that in any of the above structures, mechanical properties of the material can be altered by changing the density or texture of the material. The fibers used to make the reinforcing component can be for example, monofilaments, yarns, threads, braids, or bundles of fibers. These fibers can be made of any biocompatible material. In an exemplary embodiment, the fibers that comprise the nonwoven or three-dimensional mesh are formed of a polylactic acid (PLA) and polyglycolic acid (PGA) copolymer at a 95:5 mole ratio. Illustrated examples of the synthetic portion also include 90/10 PGA/PLA, 95/5 PLA/PGA, and polydioxanone (PDO) nonwoven mats, and perforated thin sheets of 60/40 PLA/PCL (polycaprolactone) or 65/35 PGA/PCL.

A variety of biocompatible polymers can be used to make fibers for the synthetic portion. Examples of suitable biocompatible, bioabsorbable polymers that could be used include polymers selected from the group consisting of aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amine groups, poly(anhydrides), polyphosphazenes, biomolecules and blends thereof. For the purpose of this disclosure aliphatic polyesters include but are not limited to homopolymers and copolymers of lactide (which includes lactic acid, D-,L- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate (repeating units), hydroxyvalerate (repeating units), 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, α,α-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one, copolymers, and polymer blends thereof. Other synthetic polymers are known in the art and may be used within the scope of this disclosure.

The particular polymer may be selected depending on one or more of the following factors: (a) bio-absorption (or bio-degradation) kinetics; (b) in-vivo mechanical performance; and (c) cell response to the material in terms of cell attachment, proliferation, migration and differentiation and (d) biocompatibility. With respect to the bio-absorption kinetics, it is known to control resorption rates by selection of the polymer or copolymer. By way of example, it is known that a 35:65 blend of ε-caprolactone and glycolide is a relatively fast absorbing polymer and a 40:60 blend of ε-caprolactone and (L)lactide is a relatively slow absorbing polymer. Optionally, two or more polymers or copolymers could then be blended together to form a foam having several different physical properties.

In some orthopaedic applications, it is desirable to combine the tissue remodeling properties of ECM with the controlled resorption properties of synthetic foams, mats, or sheets. Thus, methods are provided for making porous scaffolds for the repair or regeneration of a body tissue, wherein the scaffolds comprise an ECM component and a synthetic portion. According to one illustrative embodiment, there is provided a method of making an implantable scaffold for repairing damaged or diseased tissue. The method includes the steps of suspending pieces of an ECM material in a liquid and mixing a polymer solution into the liquid. The mixture is formed into a mass and, subsequently, the liquid is driven off so as to form interstices in the mass. In another embodiment, the method includes suspending pieces of an ECM material in a liquid and forming a mass. A polymer mat, for example, a mesh or nonwoven, is coated with the ECM material, and, subsequently, the liquid is driven off, forming a foam having a combination of mechanical and biological features.

In one specific implementation of an exemplary embodiment, the liquid is driven off by lyophilizing the ECM and synthetic material and the liquid in which they are suspended. In such a manner, the liquid is sublimed thereby forming the interstices in the mass.

The material density and pore size of the scaffold may be varied by controlling the rate of freezing of the suspension. The amount of water into which the pieces of extracellular matrix material are suspended may also be varied to control the material density and pore size of the resultant scaffold. Furthermore, as discussed above, the resorption rate may be controlled by varying the synthetic polymer structure or composition.

In accordance with another exemplary embodiment, there is provided an implantable scaffold for repairing or regenerating tissue prepared by the process described above.

Thus, one aspect of this disclosure is directed to a method of making an implantable scaffold for repairing or regenerating body tissue, the method comprising the steps of suspending ECM material in a liquid to form a slurry, adding a synthetic portion to the slurry to make an ECM/synthetic composition, freezing the composition to form crystals therein, and driving off the crystals to form a foam. In one illustrated embodiment, the ECM is comminuted. In another illustrated embodiment, the liquid is water, the crystals are ice, and the crystals are driven off by lyophilization.

In another aspect of this disclosure an implantable scaffold for repairing or regenerating body tissue is provided, the scaffold comprising a porous ECM foam and a synthetic mat imbedded therein.

Yet another aspect is an implantable scaffold comprising a mass of ECM intermixed with a fibrous synthetic portion in a composition dried to have a desired porosity.

Still, another aspect of this invention is an implantable scaffold comprising a porous foam comprising ECM and a synthetic portion distributed within the foam.

The above and other features of the present disclosure will become apparent from the following description and the attached drawings.

BRIEF DESCRIPTION OF THE DRAWINGS

The detailed description particularly refers to the accompanying figures in which.

DETAILED DESCRIPTION OF THE DISCLOSURE

Figure 1:
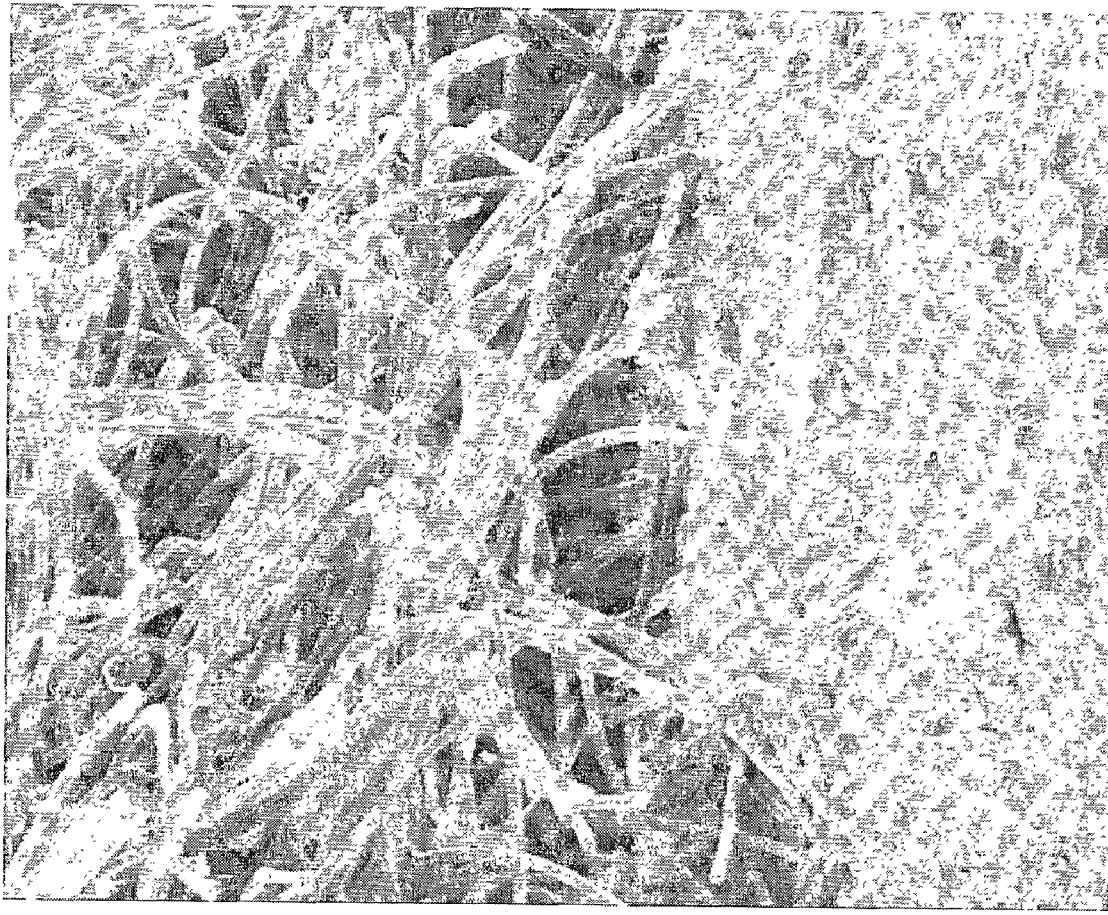
FIG. 1 is a scanning electron micrograph showing the surface of a porous three-dimensional SIS/synthetic polymer hybrid scaffold comprising a nonwoven, needled VICRYL® sheet (Ethicon, Inc, Somerville, N.J.) coated with SIS foam. Wet SIS slurry was coated on the VICRYL® sheet, and the assembly was needled and then lyophilized.

The present disclosure relates to porous scaffolds for implanting into the body of a patient to repair or regenerate damaged or diseased tissue. The porous scaffold is constructed from a naturally occurring extracellular material and a synthetic polymer. For example, the scaffold may be constructed from a mat of mesh or nonwoven synthetic material coated with SIS, a mixture of SIS and a synthetic polymer, or from layers of SIS and synthetic polymer. The material density, pore size, and resorption rate of the porous scaffold may be varied to fit the needs of a given scaffold design.

Such porous scaffolds may be fabricated by first suspending pieces of an ECM material in a liquid. As used herein, the term "suspending" is intended to include any placement of a solid (e.g., pieces of ECM) in a liquid whether or not an actual suspension is created. As such, the term "suspending" is intended to include any mixing of a solid in a liquid or any other placement of a solid in a liquid. As a result, the term "suspension" is likewise not intended to be limited to suspensions, but rather is intended to mean any mass having a solid present in a liquid. Suspension of the pieces of ECM material in the liquid forms a mass in the form of, for example, a "slurry". The slurry may be used to coat a mat of mesh or nonwoven synthetic portion or a solution of a synthetic polymer may be added to the slurry, and the liquid may then be subsequently driven off of so as to form interstices therein. The liquid may be driven off in a number of different manners. For example, as will herein be described in greater detail, the liquid may be driven off via sublimation in a freeze drying process. Alternatively, the liquid may also be driven off by subjecting the suspension to vacuum under a controlled heating process. The liquid may also be driven off from the suspension ultrasonically. Microwave energy may also be utilized to drive the liquid off of the suspension. Moreover, the liquid may include a water-soluble filler that is driven off, for example, by use of an alcohol.

While any of the aforementioned processes for driving off the liquid from the suspension may be used, along with any other process known by one skilled in the art, the processes of the present disclosure will herein be exemplary described in regard to a lyophilization process (i.e., freeze drying). However, it should be understood that such a description is merely exemplary in nature and that any one or more of the afore-described processes for driving off the liquid from the suspension may be utilized to fit the needs of a given scaffold design or process design.

As discussed above, one useful process for fabricating the porous scaffolds of the present disclosure is by lyophilization. In this case, an ECM/polymer composition is frozen and subsequently lyophilized. Freezing the suspension causes the liquid to crystallize. These crystals are then sublimed during the lyophilization process, thereby leaving interstices in the material in the spaces previously occupied by the crystals. The material density and pore size of the resultant scaffold may be varied by controlling, among other things, the rate of freezing of the suspension and/or the amount of water in which the ECM material is suspended in at the start of the freezing process.

As a specific example of this process, fabrication of porous SIS/synthetic hybrid scaffolds by lyophilization will be described in detail. However, it should be appreciated that although the example is herein described in regard to an SIS/synthetic scaffold, fabrication of a scaffold constructed from other ECM materials and synthetic polymers may also be performed in a similar manner.

The first step in fabricating a porous scaffold with a desired pore size and density is the procurement of comminuted SIS. Illustratively, scissor-cut SIS runners (~6" long) are positioned in a 1700 series COMITROL® machine, commercially available from Urschel Laboratories (Valpraiso, Ind.). The SIS material is processed and thereafter collected in a receptacle at the output of the machine. The material is then processed through the machine a second time under similar conditions. The resultant material is a "slurry" of SIS material (thin, long SIS fibers ~200 microns thick×1-5 mm long) suspended in a substantially uniform manner in water. Although the suspension is herein described as being formed as a byproduct of the comminuting process, it should be appreciated that the pieces of SIS may be suspended in the liquid (i.e., water) in other manners known to those skilled in the art. Furthermore, while other methods are known for comminuting SIS, it is understood that for the purposes of the present disclosure, comminuted SIS comprises ribbon-like or string-like fibers wherein at least some of the individual pieces of ECM and SIS material have lengths greater than their widths and thicknesses. Such fibers may be interlaced to provide a felt-like material, if desired.

Process parameters can be varied using the above-identified 1700 series COMITROL® machine, including the choice of blade used, whether water is used, the amount of water used, the speed at which the blades turn, and the number of times the material is passed through the machine. As an example, cutting head 140084-10 and a VERICUT®, sealed impeller from Urschel Laboratories may be used, with a flow of water of about two (2) gallons per minute, with the blade running at a constant speed of about 9300 rpm. A first pass through the machine at these parameters will produce fibrous SIS material of varying sizes, and a second pass will produce SIS fibers of a more uniform size. By way of example, the comminuted material may be tested to determine if it has the consistency of that which is desired for use in regard to the illustrative embodiments described herein by the following process: the comminuted SIS suspension or slurry is centrifuged, excess water is poured off and the remaining slurry is poured into a dish. By hand, a small amount of the comminuted SIS material in the dish is pinched between the thumb and index finger and gently lifted from the dish. Illustratively, at least a small amount of additional SIS, beyond the portion pinched between the thumb and index finger, will lift along with the material that has been pinched. This additional comminuted SIS material lifts with the material that is between the thumb and index finger because the individual pieces of comminuted SIS material are comingled or intertwined. Prior art methods of "comminuting" SIS using a freezer mill produce particles, rather then ribbon-like fibers. The prior art particles are not capable of significant intertwining and, for purposes of the present disclosure, are not included within the definition of comminuted SIS. See copending U.S. patent application Ser. No. 10/195,354 entitled "Porous Extracellular Matrix Scaffold and Method".

The terms "cohesive ECM", "cohesive SIS", "cohesive ECM pieces" and "cohesive SIS pieces" are used herein to respectively denote ECM or SIS material that has been comminuted or otherwise physically processed to produce ECM or SIS pieces that are capable of comingling or intertwining (in the wet or dry state) to form a mass of discrete pieces of ECM or SIS that remain massed together under some conditions (such as under gravity), regardless of the shape or shapes of the individual ECM or SIS pieces. One method of demonstrating that the ECM or SIS material comprises cohesive pieces is the "pinch test" described in the preceding paragraph. Examination of the final ECM or SIS product produced may also provide evidence that the base material comprised cohesive ECM or SIS pieces. Illustratively, the ECM or SIS pieces are sufficiently cohesive to each other (or to other pieces in the mix or slurry) that they remain unified throughout the process used to produce the foam structure.

A polymer solution is also prepared, as is known in the art. By way of example, a 95:5 weight ratio solution of 60/40 PLA/PCL is made and poured into a flask. The flask is placed in a water bath, stirring at 60-70° C. for 5 hrs. The solution is filtered using an extraction thimble, extra coarse porosity, type ASTM 170-220 (EC) and stored in flasks.

Thereafter, the comminuted SIS suspension is mixed or layered with the polymer solution. In another embodiment, the SIS suspension is used with or without an intermixed polymer solution to coat a mat of mesh or nonwoven polymer. The SIS/polymer composition is frozen and lyophilized (i.e., freeze dried). In particular, the SIS/polymer composition is frozen at a controlled rate of temperature drop to control the size of the formed crystals. Once frozen, and without allowing the material to thaw, the lyophilization process sublimes the crystals directly to a vapor under vacuum and low temperatures. This leaves voids or interstices in the spaces previously occupied by the crystals. In the embodiments wherein the polymer component is a mat of mesh or nonwoven material, the SIS forms a foam around the polymer component, and, depending on the size of the interstices, the foam may form therethrough.

Any method for freezing the composition to a desired temperature may be used Likewise, any commercially available lyophilizer may be used for the lyophilization process. One exemplary machine for performing the lyophilization process is a Virtis GENESIS™ Series lyophilizer that is commercially available from SP Industries, Inc. (Gardiner, N.Y.).

The process parameters of the aforedescribed fabrication process may be varied to produce scaffolds of varying pore sizes and material densities. For example, the rate at which the suspension is frozen, the amount of water present in the suspension, and the compactness of the ECM material each may be varied to produce scaffolds of varying pore sizes and material densities.

For instance, to produce scaffolds having a relatively large pore size and a relatively low material density, the composition may be frozen at a slow, controlled rate (e.g., −1° C./min or less) to a temperature of about −20° C., followed by lyophilization of the resultant mass. To produce scaffolds having a relatively small pore size and a relatively high material density, the SIS suspension may be tightly compacted by centrifuging the material to remove a portion of the liquid (e.g., water) in a substantially uniform manner prior to mixing with the polymer component. If desired, the fibers of the hybrid foams may be crosslinked, for example physically, chemically, or enzymatically, to increase mechanical strength of the scaffold.

Additionally, because of the porosity of the scaffolds, the scaffolds of the present disclosure may be used to deliver various biologically active agents to a damaged tissue, in addition to those already present in the ECM, including one or more exogenous biologically-derived agents or substances, one or more cell types, one or more biological lubricants, one or more biocompatible inorganic materials, one or more biocompatible synthetic polymers and one or more biopolymers. Various biologically active agents can be added to the foams, for example, prior to lyophilization, or subsequent to lyophilization by adsorption onto the surface or back filling into the foams after the foams are made. For example, the pores of the foam may be partially or completely filled with biocompatible resorbable synthetic polymers or biopolymers (such as collagen or elastin) or biocompatible inorganic materials (such as hydroxyapatite) and combinations thereof.

"Bioactive agents" include one or more of the following: chemotactic agents; therapeutic agents (e.g. antibiotics, steroidal and non-steroidal analgesics and anti-inflammatories, anti-rejection agents such as immunosuppressants and anti-cancer drugs); various proteins (e.g. short chain peptides, bone morphogenic proteins, glycoprotein and lipoprotein); cell attachment mediators; biologically active ligands; integrin binding sequence; ligands; various growth and/or differentiation agents (e.g. epidermal growth factor, IGF-I, IGF-II, TGF-β I-III, growth and differentiation factors, vascular endothelial growth factors, fibroblast growth factors, platelet derived growth factors, insulin derived growth factor and transforming growth factors, parathyroid hormone, parathyroid hormone related peptide, bFGF; TGF$_\beta$ superfamily factors; BMP-2; BMP-4; BMP-6; BMP-12; sonic hedgehog; GDF5; GDF6; GDF8; PDGF); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate; DNA fragments and DNA plasmids. If other such substances have therapeutic value in the orthopaedic field, it is anticipated that at least some of these substances will have use in the present invention, and such substances should be included in the meaning of "bioactive agent" and "bioactive agents" unless expressly limited otherwise.

"Biologically derived agents" include one or more of the following: bone (autograft, allograft, and xenograft) and derivates of bone; cartilage (autograft, allograft, and xenograft), including, for example, meniscal tissue, and derivatives; ligament (autograft, allograft, and xenograft) and derivatives; derivatives of intestinal tissue (autograft, allograft, and xenograft), including for example submucosa; derivatives of stomach tissue (autograft, allograft, and xenograft), including for example submucosa; derivatives of bladder tissue (autograft, allograft, and xenograft), including for example submucosa; derivatives of alimentary tissue (autograft, allograft, and xenograft), including for example submucosa; derivatives of respiratory tissue (autograft, allograft, and xenograft), including for example submucosa; derivatives of genital tissue (autograft, allograft, and xenograft), including for example submucosa; derivatives of liver tissue (autograft, allograft, and xenograft), including for example liver basement membrane; derivatives of skin tissue; platelet rich plasma (PRP), platelet poor plasma, bone marrow aspirate, demineralized bone matrix, insulin derived growth factor, whole blood, fibrin and blood clot. Purified ECM and other collagen sources are also intended to be included within "biologically derived agents." If other such substances have therapeutic value in the orthopaedic field, it is anticipated that at least some of these substances will have use in the present invention, and such substances should be included in the meaning of "biologically derived agent" and "biologically derived agents" unless expressly limited otherwise.

"Biologically derived agents" also include bioremodelable collageneous tissue matrices. The expressions "bioremodelable collagenous tissue matrix" and "naturally occurring bioremodelable collageneous tissue matrix" include matrices derived from native tissue selected from the group consisting of skin, artery, vein, pericardium, heart valve, dura mater, ligament, bone, cartilage, bladder, liver, stomach, fascia and intestine, tendon, whatever the source. Although "naturally occurring bioremodelable collageneous tissue matrix" is intended to refer to matrix material that has been cleaned, processed, sterilized, and optionally crosslinked, it is not within the definition of a naturally occurring bioremodelable collageneous tissue matrix to purify the natural fibers and reform a matrix material from purified natural fibers. The term "bioremodelable collageneous tissue matrices" includes "extracellular matrices" within its definition.

"Cells" include one or more of the following: chondrocytes; fibrochondrocytes; osteocytes; osteoblasts; osteoclasts; synoviocytes; bone marrow cells; mesenchymal cells; stromal cells; stem cells; embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. If other cells are found to have therapeutic value in the orthopaedic field, it is anticipated that at least some of these cells will have use in the present invention, and such cells should be included within the meaning of "cell" and "cells" unless expressly limited otherwise. Illustratively, in one example of embodiments that are to be seeded with living cells such as chondrocytes, a sterilized implant may be subsequently seeded with living cells and packaged in an appropriate medium for the cell type used. For example, a cell culture medium comprising Dulbecco's Modified Eagles Medium (DMEM) can be used with standard additives such as non-essential amino acids, glucose, ascorbic acid, sodium pyrovate, fungicides, antibiotics, etc., in concentrations deemed appropriate for cell type, shipping conditions, etc.

"Biological lubricants" include: hyaluronic acid and its salts, such as sodium hyaluronate; glycosaminoglycans such as dermatan sulfate, heparan sulfate, chondroiton sulfate and keratan sulfate; synovial fluid and components of synovial fluid, including mucinous glycoproteins (e.g. lubricin), tribonectins, articular cartilage superficial zone proteins, surface-active phospholipids, lubricating glycoproteins I, II; vitronectin; and rooster comb hyaluronate. "Biological lubricant" is also intended to include commercial products such as ARTHREASE™ high molecular weight sodium hyaluronate, available in Europe from DePuy International, Ltd. of Leeds, England, and manufactured by Bio-Technology General (Israel) Ltd., of Rehovot, Israel; SYNVISC® Hylan G-F 20, manufactured by Biomatrix, Inc., of Ridgefield, N.J. and distributed by Wyeth-Ayerst Pharmaceuticals of Philadelphia, Pa.; HYLAGAN® sodium hyaluronate, available from Sanofi-Synthelabo, Inc., of New York, N.Y., manufactured by FIDIA S.p.A., of Padua, Italy; and HEALON® sodium hyaluronate, available from Pharmacia Corporation of Peapack, N.J. in concentrations of 1%, 1.4% and 2.3% (for ophthalmologic uses). If other such substances have therapeutic value in the orthopaedic field, it is anticipated that at least some of these substances will have use in the present invention, and such substances should be included in the meaning of "biological lubricant" and "biological lubricants" unless expressly limited otherwise.

"Biocompatible polymers" is intended to include both synthetic polymers and biopolymers (e.g. collagen). Examples of biocompatible polymers include: polyesters of [alpha]-hydroxycarboxylic acids, such as poly(L-lactide) (PLLA) and polyglycolide (PGA); poly-p-dioxanone (PDO); polycaprolactone (PCL); polyvinyl alcohol (PVA); polyethylene oxide (PEO); polymers disclosed in U.S. Pat. Nos. 6,333,029 and 6,355,699; and any other bioresorbable and biocompatible polymer, co-polymer or mixture of polymers or co-polymers that are utilized in the construction of prosthetic implants. In addition, as new biocompatible, bioresorbable materials are developed, it is expected that at least some of them will be useful materials from which orthopaedic devices may be made. It should be understood that the above materials are identified by way of example only, and the present invention is not limited to any particular material unless expressly called for in the claims.

"Biocompatible inorganic materials" include materials such as hydroxyapatite, all calcium phosphates, alpha-tricalcium phosphate, beta-tricalcium phosphate, calcium carbonate, barium carbonate, calcium sulfate, barium sulfate, polymorphs of calcium phosphate, sintered and non-sintered ceramic particles, and combinations of such materials. If other such substances have therapeutic value in the orthopaedic field, it is anticipated that at least some of these substances will have use in the present invention, and such substances should be included in the meaning of "biocompatible inorganic material" and "biocompatible inorganic materials" unless expressly limited otherwise.

It is expected that various combinations of bioactive agents, biologically derived agents, cells, biological lubricants, biocompatible inorganic materials, biocompatible polymers can be used with the devices of the present invention.

EXAMPLE 1

An aqueous suspension of SIS ("slurry") is made, of approximately 8 mg dry weight of comminuted SIS material per mL of water. The slurry is placed within a beaker on a stirring plate for approximately 3 minutes to ensure that the SIS is evenly dispersed in the suspension.

A polymer solution of 95:5 weight ratio solution of 60/40 PLA/PCL is made and poured into a flask. The flask is placed in a water bath, stirring at 60-70EC for 5 hrs. The solution is filtered using an extraction thimble, extra coarse porosity, type ASTM 170-220 (EC) and stored in flasks.

An equal amount of the polymer solution is added to the SIS slurry, to form an SIS/polymer mixture. The mixture is stirred on a stirring plate to make sure that the SIS and polymer are evenly dispersed in the suspension.

The porous scaffolds are obtained by freezing a comminuted SIS suspension at a slow, controlled rate (−1° C./min or less) to −20° C., followed by lyophilization, as follows: a slow-freeze ethanol bath is prepared by pouring enough ethanol to obtain about a 1 centimeter head in a flat-bottomed plastic container large enough to hold four 24-well culture plates. The container is placed in a −20° C. freezer. Under a sterile hood using sterile conditions, an approximately 3 ml aliquot of the comminuted SIS/polymer material is placed in each well of the tissue culture plates. The culture plates are then placed into the ethanol freeze bath and allowed to freeze overnight.

The frozen plates are then removed from the ethanol bath and placed in a suitable lyophilizer, such as the Virtis GENESIS™ Series lyophilizer described above. The parameters used in the lyophilization process include a first period at a primary drying temperature of 13° C. for 8 hours, followed by a second period at a secondary drying temperature of 35° C. for 4 hours.

The resulting foam may be shaped or sculpted for the particular application. It is also understood that the mold could be provided in the desired shape, reducing or obviating the need for sculpting or trimming.

While Example 1 is directed to porous SIS/polymer scaffolds having a relatively large pore size, it is understood that the freezing and lyophilization profiles may be adjusted to produce scaffolds of desired size. Copending U.S. application Ser. No. 10/195,354 entitled "Porous Extracellular Matrix Scaffold and Method", already incorporated by reference, provides various freezing and lyophilization profiles for the control of porosity.

EXAMPLE 2

An SIS slurry and a polymer solution are prepared as in Example 1. However, rather than mixing a solution of polymer with the SIS, the solution of the polymer is layered over the mass. The layered mixture is then frozen and lyophilized as in Example 1, forming a foam having several layers of different mechanical and biological composition. However, because the foam layers are formed together and expand somewhat into the interstices of the adjacent layer, there would not be a discrete demarcation between the synthetic foam and the ECM foam. Allowing the layers to mix slightly prior to lyophilization will increase the width of the transition zone between the layers.

EXAMPLE 3

In this example, a layered construct is formed wherein the scaffold has an SIS foam component and a synthetic mat component.

An SIS slurry is prepared as in Example 1. Next, a 2 cm×2 cm piece of a 90/10 PGA/PLA mat is presoaked in water and then placed in the beaker with the SIS slurry. The 90/10 PGA/PLA piece is fully immersed within the slurry, resulting in an SIS-coated mat, having a thick coating of the SIS material on the synthetic mat. Several such SIS-coated 90/10 PGA/PLA mats are prepared. The coated mats are immediately transferred to a −80° C. freezer. After freezing, the coated mats are lyophilized as in Example 1.

While 90/10 PGA/PLA is used for the mat in this example, it is understood that the additional structural component can be made of any biocompatible material, including bioabsorbable materials such as polylactic acid (PLA), polyglycolic acid (PGA), polycaprolactone (PCL), polydioxanone (PDO), trimethylene carbonate (TMC), polyvinyl alcohol (PVA), copolymers or blends thereof. Furthermore, it is understood that additional structure may be provided by a variety of woven and nonwoven felts, meshes, textiles or other materials. As with the synthetic foam component, the composition of the additional structural component may be selected to provide an appropriate resorption rate.

EXAMPLE 4

Figure 2:
FIG. 2 is a scanning electron micrograph showing the surface of a porous three-dimensional SIS/synthetic polymer hybrid scaffold in which the SIS portion is sandwiched between two nonwoven VICRYL® The assembly was needled and then lyophilized.

An SIS-coated 90/10 PGA/PLA mat is prepared as in Example 3. The SIS-coated 90/10 PGA/PLA mat is "needled" using stainless steel needle pad (having a plastic base with several closely spaced, about 1 mm apart, stainless steel needles). The needling procedure involved applying the wet hybrid implant to the needle pad and applying thumb pressure to drive the needles through the thickness of the implant. The needling is believed to enhance mechanical entangling between the synthetic and SIS portions of the hybrid scaffold, resulting in between adherence of the layers. The implant is then transferred to the −80° C. freezer, and subsequently lyophilized, as in Example 3. FIG. 1 shows a similar foam made with a VICRYL® mat. FIG. 2 is also similar, having several layers of VICRYL®.

EXAMPLE 5

Figure 3:
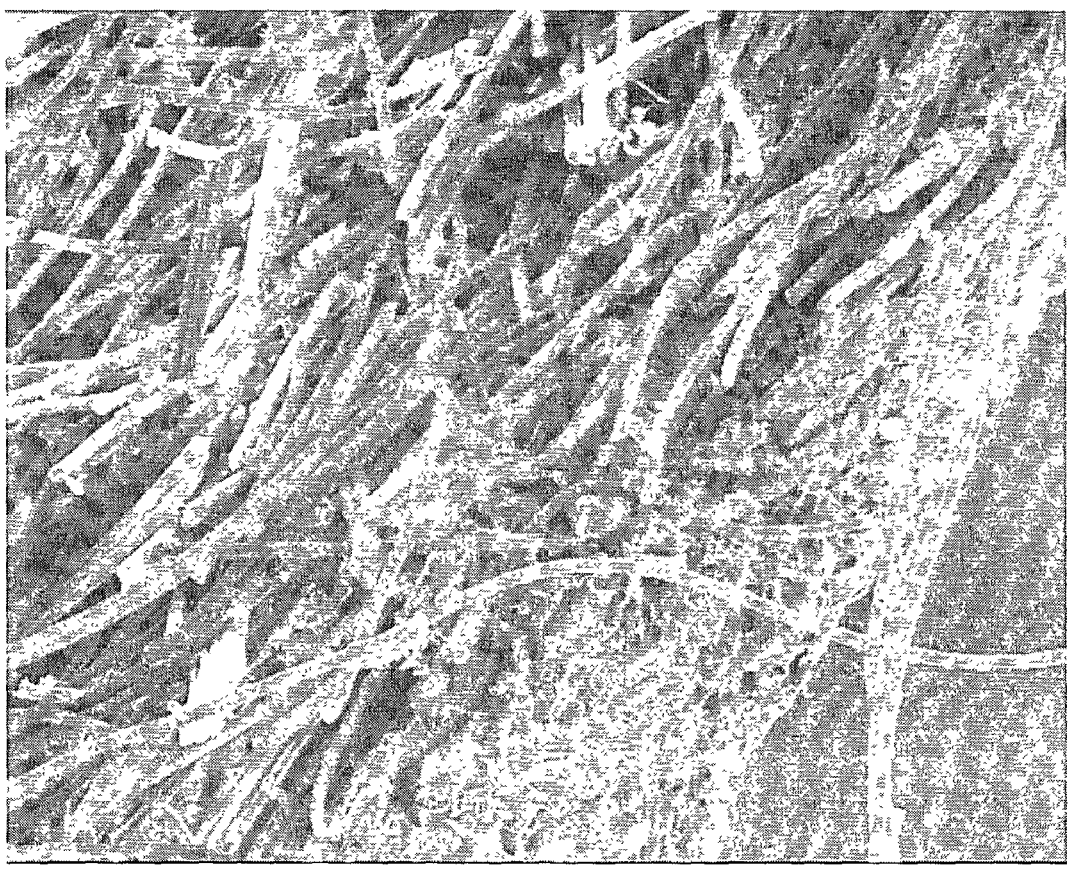
FIG. 3 is a scanning electron micrograph showing the surface of a porous three-dimensional SIS/synthetic polymer hybrid scaffold comprising a nonwoven, non-needled VICRYL® sheet coated with SIS foam. Wet SIS slurry was coated on the VICRYL® sheet. The construct was centrifuged, additional SIS slurry was added, followed by additional centrifugation. The construct was needled and then lyophilized.

An SIS slurry is prepared as in Example 1. 2 cm diameter 90/10 PGA/PLA mats are placed into individual wells of a six well tissue culture plate. 4 mL of the SIS slurry is pipetted onto each 90/10 PGA/PLA mat. The plate is centrifuged at 2000 rpm for 2 minutes. The water is decanted off and another 2 mL of the slurry is added and the plates are centrifuged in the same way. This treatment resulted in an approximately 1 mm thick coating of SIS on the 90/10 PGA/PLA disk. Some of these implants are needled in the same way as described in Example 4. Others were not needled at all. The implants are then frozen and lyophilized as described in Example 3. FIG. 3 shows a similar foam using VICRYL®.

As can be seen from the forgoing description, the concepts of the present disclosure provide numerous advantages. For example, the concepts of the present disclosure provide for the fabrication of a porous implantable scaffold which may have varying mechanical properties to fit the needs of a given scaffold design. For instance, the pore size and the material density may be varied to produce a scaffold having a desired mechanical configuration. In particular, such variation of the pore size and the material density of the scaffold is particularly useful when designing a scaffold which provides for a desired amount of cellular migration therethrough, while also providing a desired amount of structural rigidity. Additionally, by selecting an appropriate polymer, mechanical strength and resorption rates can be controlled, to provide mechanical support for a desired length of time subsequent to implantation.

While the disclosure is susceptible to various modifications and alternative forms, specific exemplary embodiments thereof have been shown by way of example in the drawings and has herein be described in detail. It should be understood, however, that there is no intent to limit the disclosure to the particular forms disclosed, but on the contrary, the intention is to cover all modifications, equivalents, and alternatives falling within the spirit and scope of the disclosure.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

The invention claimed is:

1. A method of making an implantable scaffold for repairing or regenerating body tissue, the method comprising the steps of:
   cutting a naturally occurring extracellular matrix in the presence of a liquid to produce a cohesive mass of intertwined strips, ribbons, or fibers;
   contacting a synthetic polymer with the cohesive mass to make a composition comprising the cohesive mass and the polymer;
   freezing the composition comprising the cohesive mass and the polymer to form a frozen composition, said frozen composition comprising crystals, and
   driving off the crystals to form a foam.

2. The method of claim 1, further comprising the step of centrifuging the cohesive mass to compact the cohesive mass prior to the step of contacting the synthetic polymer with the cohesive mass.

3. The method of claim 1, wherein the naturally occurring extracellular matrix is selected from the group consisting of small intestinal submucosa, stomach submucosa, bladder submucosa, alimentary submucosa, respiratory submucosa, genital submucosa, and liver basement membrane.

4. The method of claim 1, wherein the synthetic polymer is formed as a mat, and said contacting step comprises coating the mat with the cohesive mass to form a coated mat, prior to the freezing step.

5. The method of claim 4, wherein the coating step comprises immersing the mat in the cohesive mass.

6. The method of claim 4, wherein the coating step includes placing the cohesive mass onto the mat and centrifuging the mat.

7. The method of claim 4, further comprising the step of driving a needle into the coated mat.

8. A method of making an implantable scaffold comprising the steps of:
   comminuting a naturally occurring extracellular matrix in a liquid to form ribbon-like pieces of the naturally-occurring extracellular matrix suspended in the liquid and intertwining said ribbon-like pieces of the naturally-occurring extracellular matrix by mixing to form a cohesive naturally occurring extracellular matrix;
   contacting the cohesive naturally occurring extracellular matrix with synthetic polymers to form a composition comprising a cohesive naturally occurring extracellular matrix layer, a synthetic polymer layer and a transition zone comprising both the cohesive naturally occurring extracellular matrix and synthetic polymers;
   freezing the composition to form a frozen composition, said frozen composition comprising crystals, and
   driving off the crystals to form a foam.

9. A method of making an implantable scaffold comprising the steps of:
   cutting a naturally occurring extracellular matrix in the presence of a liquid to produce a cohesive mass of intertwined strips, ribbons, or fibers;
   coating a synthetic polymer mat with the cohesive mass;
   freezing the coated mat to form a frozen composition, said frozen composition comprising crystals, and
   driving off the crystals to form a foam coated mat.

10. The method of claim 9, further comprising the steps of:
    mixing a composition comprising synthetic polymers with the cohesive mass; and
    coating the synthetic mat with the mixture.

11. The method of claim 8, wherein the naturally occurring extracellular matrix is selected from the group consisting of small intestine submucosa, stomach submucosa, bladder submucosa, alimentary submucosa, respiratory submucosa, genital submucosa, and liver basement membrane.

12. The method of claim 9, wherein the naturally occurring extracellular matrix is selected from the group consisting of small intestine submucosa, stomach submucosa, bladder submucosa, alimentary submucosa, respiratory submucosa, genital submucosa, and liver basement membrane.

13. The method of claim 8, further comprising the step of allowing the cohesive naturally occurring extracellular matrix layer and the synthetic polymer layer to expand and mix with each other for a length of time prior to the freezing step to increase the width of the transition zone.

14. The method of claim 1, further comprising the step of crosslinking the components of the foam.

15. The method of claim 1, wherein the driving off step is performed by lyophilization of the frozen composition comprising the cohesive mass and the polymer.

16. The method of claim 1, further comprising the step of adding an exogenous biologically active agent.

17. The method of claim 16, wherein the biologically active agent is added prior to the freezing step.

18. The method of claim 16, wherein the biologically active agent is added after the step of driving off the crystals.

19. The method of claim 1, further comprising the step of shaping the foam.

20. The method of claim 1 wherein the naturally occurring extracellular matrix comprises small intestine submucosa.

21. The method of claim 20 wherein the strips, ribbons, or fibers are about 200 microns thick and 1-5 mm long.

22. The method of claim 8 further comprising the step of centrifuging the cohesive naturally occurring extracellular matrix, removing the supernatant, and contacting the resulting compacted, cohesive naturally occurring extracellular matrix with the synthetic polymer-comprising composition.

23. The method of claim 9 further comprising the step of centrifuging the cohesive mass, removing the supernatant, and mixing the resulting compacted, cohesive mass with the synthetic polymer mat.

24. The method of claim 8, further comprising the step of crosslinking the components of the foam.

25. The method of claim 9, further comprising the step of crosslinking the components of the foam.

26. The method of claim 8, wherein the driving off step is performed by lyophilization of the frozen composition.

27. The method of claim 8, further comprising the step of adding an exogenous biologically active agent.

28. A method of making an implantable scaffold for repairing or regenerating body tissue, the method comprising the steps of:

i) obtaining small intestine submucosa from an animal;

ii) placing said small intestine submucosa into water;

iii) cutting said small intestine submucosa into strips or fibers, wherein said strips or fibers intertwine;

iv) contacting a synthetic polymer with said intertwined strips of small intestine submucosa to produce a composition comprising said synthetic polymer and said intertwined strips of small intestine submucosa; and v) freeze-drying said composition to yield an implantable scaffold.

* * * * *